United States Patent [19]
Gilby et al.

[11] Patent Number: 5,184,192
[45] Date of Patent: Feb. 2, 1993

[54] PHOTOMETRIC APPARATUS WITH A FLOW CELL COATED WITH AN AMORPHOUS FLUOROPOLYMER

[75] Inventors: Anthony C. Gilby, Foxborough; William W. Carson, Hopkinton, both of Mass.

[73] Assignee: Millipore Corporation, Bedford, Mass.

[21] Appl. No.: 731,677

[22] Filed: Jul. 17, 1991

[51] Int. Cl.[5] ............... G01N 21/05; B29C 39/02
[52] U.S. Cl. ............... 356/246; 138/DIG. 3; 250/576; 264/1.7; 264/317
[58] Field of Search ............... 356/246, 440; 250/576; 385/125; 138/DIG. 3; 264/1.5, 1.7, 263, 317

[56] References Cited

U.S. PATENT DOCUMENTS

| | | | |
|---|---|---|---|
| 4,260,257 | 4/1981 | Neeley et al. | 356/246 |
| 4,816,123 | 3/1989 | Ogan et al. | 264/317 X |
| 5,061,024 | 10/1991 | Keys | 359/350 |

Primary Examiner—Vincent P. McGraw
Attorney, Agent, or Firm—Paul J. Cook; Andrew T. Karnakis

[57] ABSTRACT

A flow cell for optically analyzing a liquid sample is coated with a fluoropolymer having a refractive index less than the refractive index of water.

7 Claims, 1 Drawing Sheet

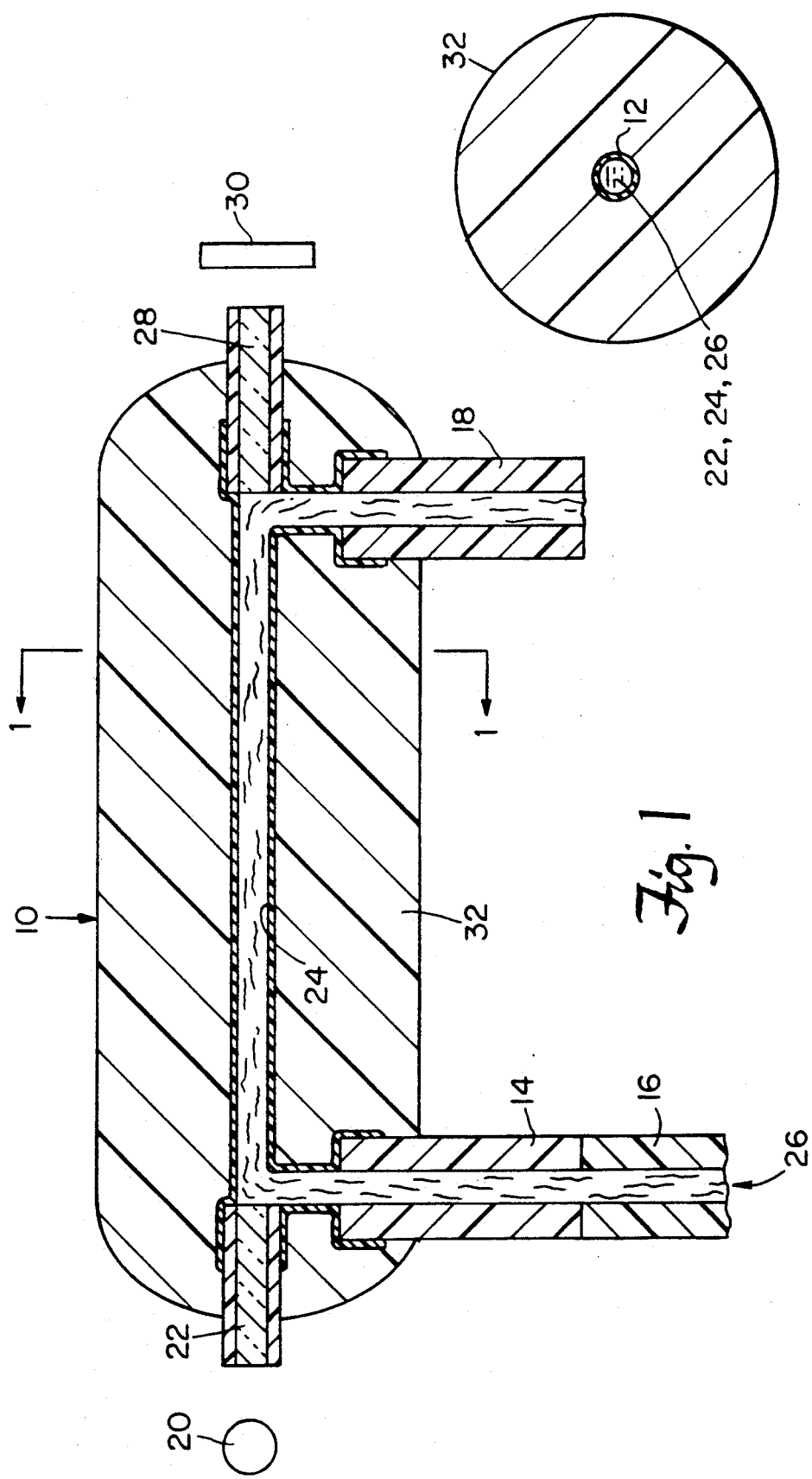

PHOTOMETRIC APPARATUS WITH A FLOW CELL COATED WITH AN AMORPHOUS FLUOROPOLYMER

BACKGROUND OF THE INVENTION

This invention relates to a photometric apparatus for spectroscopic analysis of small samples in solution. The improved apparatus includes a flow cell, uniquely suitable for aqueous solutions encountered in liquid chromatography or capillary electrophoresis, has high optical throughput, a long path length and a small cross-section.

It is well known that low concentrations of analyte in solution can be detected spectroscopically with greater sensitivity when the optical path length through the sample is long. When, as is frequently the case, the quantity of sample is limited, the optimum cell has a small cross-section. However, it is also necessary to pass sufficient optical power through the sample to maintain a good signal-to-noise ratio. The first two requirements can be met when the sample solution flows through a capillary tube of small cross-section and the optical path is along the tube axis. Large optical throughput can be achieved when the light is guided along the capillary similar to the way light is guided along an optical fiber.

Two possibilities exist for guiding light along a capillary. First, by total internal reflection at the boundary between the liquid and the capillary wall, and second, by total internal reflection between the outside diameter of the capillary and the surrounding air. In either case the tubing material must be transparent over the wavelength range of interest. The first approach is preferred, since light is confined to the liquid sample, but there is a serious limitation. The refractive index of the liquid sample must be significantly above that of the tube material, otherwise the light will pass out of the liquid into the tubing wall. Stone, in U.S. Pat. No. 3,814,497 using high-index chlorinated organic liquids and silica tubes demonstrated efficient optical transmission in the visible and near infrared wavelengths and shows a sensitive cell for Raman spectroscopy, in U.S. Pat. No. 3,770,350. X.Xi and E.S. Yeung, Anal. Chem. 1990, 62, page 1580, describes sensitive absorbance detection in capillary liquid chromatography using silica tubes and a high-index mobile phase.

Most high performance liquid chromatography (HPLC), capillary LC and capillary electrophoresis (CE) separations are done in aqueous media. The refractive index of water over the visible and ultraviolet (UV) spectral range is much less than that of fused silica which is the only existing capillary tube material to combine good sample compatibility with optical transparency to wavelengths below 200 nm. For example, at the sodium D line, 589 nm, the indices of water and fused silica are 1.333 and 1.458. Both indices rise towards the UV. At 254 nm they are 1.374 and 1.505. Thus for the majority of liquid chromatographic or CE applications, light can not be guided in the liquid along a fused silica capillary tube to achieve the desired level of sensitivity.

The index of conventional fluoropolymer (Teflon) materials, while still higher than water, is closer to it than is fused silica. For example, the index of Teflon PFA in the visible is 1.34 to 1.35. Teflon fluoropolymer tubes (FEP, PFA or PTFE) have been used with higher-index aqueous salt solutions to transmit power, as shown by Nath, U.S. Pat. No. 4,009,382, and as a colorimeter cell, as shown by Uffenheimer, U.S. Pat. No. 3,954,341. Adding solutes to elevate the refractive index would be an undesirable requirement for many chromatographic or CE separations. The use of conventional Teflon materials for an axially-illuminated detector cell has a more serious drawback—poor transparency at shorter UV wavelengths where its partial crystallinity scatters light. UV measurements down to 200 nm and below are not possible The second approach to guiding light along a capillary tube overcomes the refractive index and UV transparency limitations discussed above. Long capillary cells have been constructed of fused silica, where light guiding occurs at the boundary between the silica tube outside diameter and air. Because of the large refractive index difference between silica and air, this is a very efficient light guide of large numerical aperture, as long as the outside diameter of the silica is clean and smooth. Unfortunately, the light spends much of its time in the capillary walls, making periodic passes through the sample in the lumen. Thus, only a fraction of the optical path length is effective for analytical purposes. When light is guided at the tube outside diameter/air interface, much of the light which can be guided follows helical paths which never come into contact with the sample. This light merely adds noise to the measurement, further degrading the detector's sensitivity. An example of light guiding at the outer wall/air interface of a transparent tube is disclosed by Carlson in U.S. Pat. No. 4,477,186.

Thus, all presently available long path cells for spectroscopic detection of low concentrations and small quantities of an analyte in aqueous solution have major drawbacks and limitations. Accordingly, it would be desirable to provide an improved liquid flow cell of small cross-section and long path where light is guided axially along its length and confined to the liquid sample. Such a cell should perform well with small quantities of solute in water or aqueous solvents common in reverse phase HPLC, capillary LC or CE.

SUMMARY OF THE INVENTION

The present invention enables light to be guided axially along a liquid filled tube or capillary, independent of the wall material of the tube, the internal surface of the tube is coated with a thin layer of a class of amorphous fluoropolymers identified as Teflon AF. These polymers have a unique combination of properties; a refractive index in the visible as low as 1.29 and, because of the lack of crystallinity, UV transparency far superior to conventional polymeric materials.

Presently, Teflon AF is both very expensive and unavailable in the form of tubing. However, it has been discovered in accordance with this invention that a tube can be created with a smooth internal bore consisting of a thin layer of a Teflon AF, fluoropolymer a few wavelengths or more thick, sufficient to contain the evanescent wave of the totally-reflected light. A variety of tube substrates can be used, leaving much design flexibility, and the thin layer of Teflon AF fluoropolymer minimizes material costs.

The combination of low index (which creates an optical wave guide of large numerical aperture and therefore high optical throughput even with aqueous samples), and excellent transparency to 200 nm and below, allow as the formation of an efficient, axially-illuminated flow cell for visible/ultraviolet absorbance measurements. This cell construction improves the efficiency of fluorescence or Raman spectroscopy as well. The cell is axially-illuminated at the excitation wavelength. Fluorescent or Raman-shifted light is guided within the cell, exiting from both ends as a strong signal for spectroscopic analysis.

BRIEF DESCRIPTION OF THE DRAWINGS

FIG. 1 illustrates the photometric analysis system of this invention.

FIG. 2 is a cross-sectional view of the flow cell of FIG. 1 along line 2—2.

DESCRIPTION OF SPECIFIC EMBODIMENTS

The present invention will be described herein with reference to an absorbance flow cell for a separation column such as HPLC, capillary LC or capillary electrophoresis. However, it is to be understood that the same basic construction can be used for fluorescence or Raman spectroscopy or colorimetry, with flowing or static samples.

In accordance with this invention, a flow cell is provided comprising a tubular conduit, having the inner surface formed of a transparent amorphous fluoropolymer having a refractive index significantly less than the refractive index of water over the visible and ultraviolet spectral range. Examples of such fluoropolymers are Teflon ® AF 1600 fluoropolymer with a refractive index of 1.31 at the sodium D line and Teflon ® AF 2400 fluoropolymer with an index of 1.29. The refractive index of water at this wavelength is 1.333. At ultraviolet wavelengths, the indices of both water and the fluoropolymers increase, but the index of the water remains higher.

In one embodiment, the fluoropolymer is coated onto the inside diameter of the conduit by filling it with a solution of the Teflon AF fluoropolymer in any of several fluorinated solvents, and slowly evaporating the solvent at reduced pressure. Baking the conduit above the glass transition temperature of the Teflon AF fluoropolymer (which is 240° C. for the Teflon AF 2400 fluoropolymer) produces a smooth and transparent film, bonded to the surface. The coating is preferably at least several wavelengths thick, to prevent a significant portion of the evanescent wave associated with internally-reflected light from reaching the conduit material, where light would be lost by refraction, scattering or absorption. Optical fibers are sealed to the ends of the conduit, and flow ports are provided through small holes in the wall near the conduit ends to introduce and remove the sample. Flow may alternatively be introduced through an annular space between the fibers and the conduit inside diameter. Optical windows can be used instead of the fibers, and fluidic ports can be provided as passages in the window-sealing gaskets.

In an alternative method of construction a smooth-surfaced tube of soluble material is bent in the form of a U with a straight section for the optical cell and two legs to connect to the fluid ports. This tube is coated on its outside surface with a Teflon AF fluoropolymer and encapsulated in a high-temperature sealing composition such as an epoxy composition to impart strength. Optical fibers and capillary tubes are butted to the soluble tube before coating, so that the optical and fluidic ports become an integral part of the assembly. A solvent for the tube such as an acid solution is passed through the capillary connection to dissolve the soluble tube, thereby leaving a conduit with an internal surface of Teflon AF fluoropolymer in line between the optical input and output fibers. It has been discovered that heating the assembly above the glass transition temperature of the Teflon AF fluoropolymer improves the bond to the conduit substrate and produces a smooth optical surface.

Typical inside diameters of the flow cell for HPLC, capillary LC or CE range from 0.5 mm to 0.05 mm. Cell lengths can vary from a few mm to several cms. A water-filled cell with excellent transmission through the visible and UV has been built with a path length of over a meter. For convenience in Packaging, a long capillary cell of this invention can be curved or formed into a coil, as long as the bend radius is not so small as to introduce mechanical defects or optical bending loss.

EXAMPLE I

The following illustrates the light-carrying capacity of this axially-illuminated flow cell. The typical numerical aperture (NA) of fused silica optical fiber, usable to below 200 nm, is NA=0.22. A water "core" and Teflon AF 1600 fluoropolymer "cladding" at 589 nm has an NA=0.247 and with Teflon AF 2400 fluoropolymer the NA=0.336. Numerical aperture is the sine of the halfcone angle of rays in air accepted by the light guiding structure. Thus, with no additives to the water to elevate its refractive index, the axial cell of this invention has a higher light-carrying capacity than typical UV-transmitting optical fiber.

In use the flow cell is connected to a separation column by coventional, low-dead-volume means. The input optical fiber is positioned at the exit slit of a grating monochromator so that any desired wavelength can be passed through the cell. The exit fiber is positioned in front of one half of a dual photodetector. The other half is a reference to stabilize the measurement and receives light directly from the exit slit of the monochromator via separate optical fiber. The system just described is by way of example. It will be obvious that many other components, such as a laser source, optical filters or a photodiode array detector, can be used with the cell of this invention.

Referring to the FIGS. 1 and 2, the flow cell 10, having the low refractive index fluoropolymer layer 12 of this invention includes a fluid input section 14 connected to the exit 16 of a capillary liquid chromatography or capillary electrophoresis separation column, and a fluid outlet section 18. Light from light source 20 enters input optical fiber 22 and is directed axially into the bore 24 of cell 10 through which sample stream 26 flows. The light is guided by total internal reflection at the boundary between liquid 26 and layer 12 and leaves the cell through exit optical fiber 28 to be measured by detector 30. Cell body 32 provides mechanical strength and seals for fluid connections 14 and 18 and optical fibers 22 and 28.

We claim:

1. A flow cell for housing a liquid sample and for exposing a liquid sample to light which comprises
   a conduit having a smooth inner wall formed of an amorphous fluoropolymer having a refractive index less than the refractive index of water,
   said amorphous fluoropolymer having a thickness at least as great as the wavelength of light such that when said conduit is filled with water, visible light and ultra-violet light can be transmitted along the axis of said conduit by total internal reflection, substantially without loss.

2. The flow cell of claim 1 wherein said conduit is cylindrical.

3. The flow cell of claim 1 wherein said conduit has an inner diameter between about 0.01 mm and 1.0 mm.

4. A photometric analysis system which comprises the flow cell of claim 1,
   means for introducing light axially into said flow cell,
   means for detecting light axially from said flow cell, and means for introducing a liquid sample into said flow cell.

5. The system of claim 3 wherein said sample is introduced from a liquid chromatography column.

6. The system of claim 3 wherein said sample introduction flow is effected by electromotive force.

7. A method of fabricating the cell of claim 1 comprising the steps forming a hollow tube of dissolvable material into the shape of the fluid path, positioning input and exit optical fibers adjacent to and aligned with an axis of a section of said fluid path, positioning connecting tubing of non-dissolvable material to mate with said hollow tube coating said dissolvable hollow tube, ends of said optical fibers adjacent said hollow tube and ends of said connecting tubes adjacent said hollow tube with a fluoropolymer having a refractive index less than the refractive index of water, encapsulating said fluoropolymer coated components in a non-dissolvable matrix, and passing a solution through said connecting tubing to dissolve said dissolvable tubing such that said fluoropolymer is exposed between said optical fibers to form the internal surface of said cell.

* * * * *